United States Patent [19]

Bafford et al.

[11] Patent Number: 5,679,738

[45] Date of Patent: Oct. 21, 1997

[54] AQUEOUS POLYMERIC EMULSIONS INCORPORATING POLYMERIZED UNITS OF MICHAEL ADDUCTS OF N-VINYLFORMAMIDE

[75] Inventors: Richard Anthony Bafford, Macungie; Ning Chen, Allentown; Chung-Ling Mao, Emmaus; Walter Louis Renz, Macungie; Robert Krantz Pinschmidt, Jr., Allentown, all of Pa.

[73] Assignee: Air Products and Chemicals, Inc., Allentown, Pa.

[21] Appl. No.: 489,889

[22] Filed: Jun. 13, 1995

Related U.S. Application Data

[63] Continuation-in-part of Ser. No. 246,434, May 20, 1994, Pat. No. 5,463,110.

[51] Int. Cl.⁶ .................. C08F 114/18; C08F 126/00
[52] U.S. Cl. .................. 524/555; 524/544; 526/245
[58] Field of Search .................. 524/543, 544, 524/547, 553, 555, 558, 560, 563

[56] References Cited

U.S. PATENT DOCUMENTS

| | | | |
|---|---|---|---|
| 4,205,139 | 5/1980 | Barzynski . | |
| 4,255,548 | 3/1981 | Wingard, Jr. et al. | 526/310 |
| 4,284,776 | 8/1981 | Gruber et al. | 544/400 |
| 4,319,811 | 3/1982 | Tu et al. | 351/166 |
| 4,424,314 | 1/1984 | Barzynski et al. | 525/454 |
| 4,946,762 | 8/1990 | Albert | 430/270 |
| 4,957,977 | 9/1990 | Itagaki et al. | 525/328.4 |
| 5,281,682 | 1/1994 | Cornforth et al. | 526/273 |
| 5,326,809 | 7/1994 | Bott et al. | 524/459 |

OTHER PUBLICATIONS

Becking, L., Tetrahedron Letters, 29 (23), 2797–2800 (1988).

*Primary Examiner*—Christopher Henderson
*Attorney, Agent, or Firm*—Russell L. Brewer; William F. Marsh

[57] ABSTRACT

This invention pertains to aqueous emulsions containing water insoluble, vinyl polymer particles containing polymerized Michael adduct units of N-vinylformamide and to emulsions of vinyl acetate polymers containing said Michael adducts. These latex dispersions are prepared by the emulsion polymerization of a Michael adduct of N-vinylformamide, optionally with other ethylenically unsaturated monomers, e.g., vinyl acetate.

The Michael adducts of N-vinylformamide are represented by the formula:

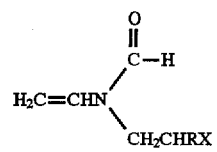

where R is H or $CH_3$, X=CN, O=$CR_1$, O=$COR_1$ or other electron withdrawing group such as $SO_3M$, $SO_3R_1$ and $NO_2$ wherein $R_1$ is a linear or branched alkyl, cycloalkyl, heterocyclic, arylalkyl, alkyloxy or aryl group containing between 1 and about 20 carbon atoms and substituted derivatives thereof and M is an ion.

The preferred Michael adduct N-vinyl amide monomers are unsaturated monomers consisting of the alkl 3-N-vinylformamidopropionates and alkyl 2-methyl-3-N-vinylformamidopropionates and represented by the formula:

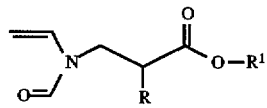

where R is hydrogen or methyl, and $R^1$ is a linear or branched alkyl, cycloalkyl, heterocyclic, arylalkyl, alkyloxy or aryl group containing between 1 and about 20 carbon atoms.

10 Claims, No Drawings

AQUEOUS POLYMERIC EMULSIONS INCORPORATING POLYMERIZED UNITS OF MICHAEL ADDUCTS OF N-VINYLFORMAMIDE

CROSS REFERENCE TO RELATED INVENTIONS

This invention is a continuation-in-part of U.S. Ser. No. 08/246,434 having a filing date of May 20, 1994 entitled Michael Adducts of N-Vinylformamide and Acrylic and Methacrylic Esters, now U.S. Pat. No. 5,463,110 which issued Oct. 31, 1995, the subject matter being incorporated by reference.

TECHNICAL FIELD OF THE INVENTION

The invention relates to aqueous emulsions which incorporate Michael adducts of N-vinylformamide.

BACKGROUND OF THE INVENTION

Unsaturated monomers of the N-vinyl amide class have been employed in free radical polymerization reactions for the preparation of homopolymers and copolymers having a range of useful properties. Of these, the N-vinyllactams, in particular N-vinyl-2-pyrrolidone, have been employed extensively owing to their wide commercial availability and rapid polymerization with a range of comonomers including the acrylic and methacrylic esters.

The following patents describe various procedures for obtaining polymer compositions formed from N-vinylamides.

U.S. Pat. No. 5,326,809 describes aqueous polymer emulsion compositions formed by the emulsion polymerization of unsaturated monomers stabilized with an amine functional water soluble polymer based on N-ethenylformamide. The water soluble amine containing polymer is formed by the polymerization of vinyl acetate and N-vinylformamide and the subsequent hydrolysis thereof.

U.S. Pat. No. 4,946,762 discloses aqueous self crosslinkable coating compositions based upon polymers formed by the polymerization of a vinyl monomer having carbonyl functional groups and amine precursor groups. Typically, the amine precursor groups are carboxyl, oxazoline or ketimine groups. Examples of carboxyl containing monomers include acrylic and methacrylic acid; maleic acid; oxazolines include 2-isopropenyl oxazoline; ethylenically unsaturated ketimines are derived by the reaction of a ketone with an amine followed by the reaction with an ethylenic derivative. The oxazolines and ketimines may be converted to amines via hydrolysis. The polymer may be prepared by emulsion polymerization.

U.S. Pat. No. 4,957,977 discloses the preparation of vinylamine copolymers and their use as flocculating agents, paper additives, etc.. The polymers are prepared by polymerizing N-vinylformamide using, mass, solution or precipitation polymerization. The formamide groups are converted to amine groups by hydrolysis in acidic aqueous medium at temperatures from 40° to 100° C.

U.S. Pat. No. 4,255,548 discloses copolymers of ethylene and vinyl amine for use as flocculants for water clarification. The polymers are formed by polymerizing ethylene and N-vinylacetamide in an alcohol medium. The resulting copolymer is then hydrolyzed by contacting the copolymer with a molar excess of aqueous mineral acid at temperatures of 75° C. and above.

U.S. Pat. No. 4,319,811 describes radiation curable coatings consisting of triacrylate or tetraacrylate monomers with an N-vinyl imido monomer, preferably an N-vinyllactam such as N-vinyl-2-pyrrolidone.

U.S. Pat. No. 5,281,682 teaches improved radiation-curable formulations containing N-vinylformamide and an oligomer selected from the group epoxy acrylates, urethane acrylates, polyester acrylates and mixtures thereof.

U.S. Pat. Nos. 4,205,139 and 4,424,314 teach curable compositions containing N-vinyl compounds in which at least two N-vinyl groups are present and in which at least one carbonyl group is bound to the nitrogen of the N-vinyl group, said carbonyl group in turn being bonded to a nitrogen or carbon atom.

U.S. Pat. No. 4,284,776 discloses radiation curable Michael adducts of amide acrylates. These compounds are formed by reacting an acrylyloxy compound with ammonia or an amine. Multifunctional acrylates are prepared by utilizing ammonia or a primary amine.

Kurtz and Disselnkoetter (*Liebigs Ann. Chem.*, 764, p. 69–93, 1972) describe the preparation of 3-N-vinylformamidopropionitrile by the reaction of N-vinylformamide with acrylonitrile in benzene utilizing a potassium cyanide catalyst. Applications for the compound are not reported. However, this material has also been found to have certain deficiencies as a photocurable monomer. A further disadvantage is the use of a highly toxic catalyst in its preparation.

SUMMARY OF THE INVENTION

This invention pertains to aqueous emulsions containing water insoluble, vinyl polymer particles containing polymerized Michael adduct units of N-vinylformamide and to latex emulsions of water insoluble polymers incorporating these adducts. They are prepared by polymerizing these adducts with ethylenically unsaturated monomers under emulsion polymerization conditions.

The Michael adducts of N-vinylformamide monomers are represented by the formula:

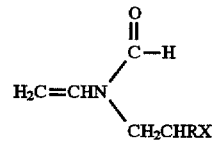

where R is H or $CH_3$, $X=CN$, $O=CR_1$, $O=COR_1$, $CNR_1R_1$, or other electron withdrawing group such as $SO_3M$, $SO_3R_1$ and $NO_2$ wherein $R_1$ is a linear or branched alkyl, cycloalkyl, heterocyclic, arylalkyl, alkyloxy or aryl group containing between 1 and about 20 carbon atoms and substituted derivatives thereof and M is an ion, typically sodium or potassium. Preferably $R_1$ is an alkyl group having from 1–12 carbon atoms or aryl. The preferred Michael adducts are unsaturated monomers consisting of the alkyl 3-N-vinylformamidopropionates and alkyl 2-methyl-3-N-vinylformamidopropionates.

There are several advantages Of polymeric emulsions which include the Michael adducts of N-vinyl amides and these include:

- an ability to produce water insoluble homopolymer and copolymer particles containing the Michael adduct of N-vinylformamide monomer incorporated in latex form;
- an ability to produce a latex containing water insoluble polymer which has excellent overall stability;
- an ability to form a latex containing water insoluble polymers having crosslinkability;

- an improved ability to effect copolymerization with a variety of vinyl monomers due to more closely matched vinyl polymerization reactivity in batch or continuous reactions;
- an ability to form vinyl ester, e.g., vinyl acetate copolymer latexes which randomly and uniformly incorporate acrylate type or nitrile functionality into the copolymer, even at high levels; and,
- an ability to generate vinyl polymers having unique properties through the use of the Michael addition products as comonomers.

DETAILED DESCRIPTION OF THE INVENTION

It has been found that Michael adducts of N-vinylformamide (NVF) can be effectively polymerized, optionally copolymerized with ethylenically unsaturated comonomers, by an emulsion polymerization process to generate amide latex polymers. Conventional emulsion polymerization of the Michael adducts of N-vinylformamide is unique and it permits the formation of a new class of polymer systems having interesting properties which are useful for adhesives, coatings, etc.

The Michael adducts used in the preparation of latex polymers are readily prepared by the nucleophilic addition of N-vinylformamide (NVF) to an alpha, beta-unsaturated monomer having an electron withdrawing group, e.g., an acrylic or methacrylic add ester. The reaction can be carried out in a simple mixture of the neat monomers, or in a solvent. NVF and the (meth)acrylate ester groups are present in the reaction mixture in molar ratio of from about 1:10 to about 20:1, and preferably at a ratio of about 1.1 moles NVF per equivalent of (meth)acrylate. A free radical inhibitor, such as benzoquinone, is also added to prevent homopolymerization of the N-vinyl amide. The reaction is preferably carried out in air, at atmospheric or other pressure.

The reaction can be described best by the reaction:

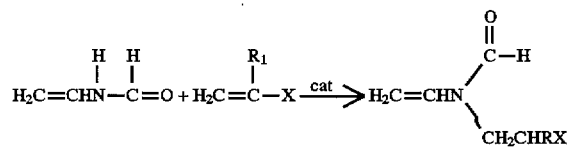

The reaction is conducted in the presence of a strongly basic catalyst such as the alkali metal or quaternary amine hydroxides or alkoxides. Bases of the methoxide, ethoxide, isopropoxide and t-butoxide class are preferred. Sodium methoxide is especially preferred. Other useful catalysts include the aryl- and alkyllithiums, potassiums and sodiums. The catalyst is present in the reaction mixture in an amount between about 0.0005 and about 5 wt. %, and preferably between 0.1 and 0.5 wt. % of the total weight of the reactants. In general, the appropriate level of catalyst will vary depending upon the equivalent weight of the (meth)acrylic ester and the molar ratio of the reactants. Following the addition of catalyst, the reactants or reactant solution are maintained at a temperature between 0° and 160° C., and preferably between 20° and 60° C.

The reagent monomers can be reacted in batch fashion, via staged addition, or continuously, whichever is more suitable. Synthesis is advantageously performed in a mixture of the neat monomers, however, an inert solvent for both reactants may be employed. Potential solvents include the amides, lower hydrocarbons, chlorinated hydrocarbons, and aromatics. Preferred solvents are esters (e.g. ethyl acetate) and ethers (e.g. diethyl ether, tetrahydrofuran).

The purified 3-N-vinylformamidopropionate adduct, for example, is preferably recovered from the reaction mixture by distillation under vacuum at between 0.01 and about 50 torr. Distillation may be performed either batchwise or continuously as, for example, in a wiped film evaporator. Other possible methods of purification include neutralization of the catalyst followed by vacuum stripping of the unreacted starting materials, or solvent extraction. In some cases, isolation of the 3-N-vinylformamido adduct from the reaction mixture may not be required. For example, the crude product may be suitable for applications in which quantities of unreacted NVF and/or (meth)acrylic ester are not problematic.

A wide range of unsaturated monomers, such as acrylic and methacrylic monomers are potentially useful as the reactant (or Michael acceptor) in this technology. These include the (meth)acrylic esters of monoalcohols having between 1 and about 20 carbon atoms, such as methyl acrylate, ethyl acrylate, propyl acrylate, n-butyl acrylate, isobutyl acrylate, t-butyl acrylate, cyanoethyl acrylate, N,N-dimethylaminoethyl acrylate, 2-ethoxyethyl acrylate, 2-hydroxyethyl acrylate, hydroxypropyl acrylate, cyclohexyl acrylate, 2-ethylhexyl acrylate, tetrahydrofurfuryl acrylate, octyl/decyl acrylate, isodecyl acrylate, lauryl acrylate, isobornyl acrylate, 2-phenoxyethyl acrylate, methyl methacrylate, and butyl methacrylate.

In addition to the monoesters described above, other coreactants for N-vinylformamide are the (meth)acrylic esters of polyhydric alcohols. Such higher functionality Michael acceptors include acrylates and methacrylates obtained by esterification of alcohols having hydroxyl functionalities from 2 to about 6. Examples of these compounds include ethyleneglycol diacrylate, 1,4-butanediol diacrylate, hexanediol diacrylate, tripropyleneglycol diacrylate, trimethylolpropane triacrylate, pentaerythritol tetraacrylate, ethyleneglycol dimethacrylate, trimethylolpropane trimethacrylate, polyethyleneglycol dimethacrylate, etc.

The N-vinylformamides can also be reacted with other reactive compounds such as vinyl ketches. An example is methyl vinyl ketone. Acrylonitrile is also another Michael addition reactive compound and it can be used to incorporate nitrile functionality into the polymer as for example a polyvinyl acetate/co-3-N-vinylformamide propionitrile.

The above reactants capable of Michael addition with N-vinylformamide may be substituted with a variety of substituents so long as the substituent is not reactive with the secondary hydrogen on the N-vinylformamide. Such reactive may interfere with the Michael reaction.

The preferred adducts include derivatives of esters of acrylic acid and methacrylic acid and are represented by the formula:

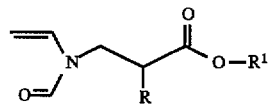

where R is hydrogen or methyl, and $R^1$ is a linear or branched alkyl, cycloalkyl, heterocyclic, arylalkyl, alkyloxy or aryl group containing between 1 and about 20 carbon atoms and substituted derivatives thereof. Specific adducts include methyl 3-(N-vinylformamido)-propionate, ethyl 3-(N-vinylformamido)-propionate, butyl 3-(N-vinylformamido)-propionate, 2-ethylhexyl 3'-(N- vinylformamido)-propionate, 3-(N-vinylformamido)-propionitrile, methyl 2-methyl-3-(N-vinylformamido)-propionate, N-acetonyl-N-vinylformamide and t-butyl 3-(N-vinylformamido)-propionate.

A variety of comonomers, e.g., ethylenically unsaturated monomers can be copolymerized with the Michael adducts of N-vinylformamide. For example, $C_1$–$C_8$ alkyl vinyl esters, $C_{1-18}$ esters and amides of acrylic acid and methacrylic acid, unsaturated carboxylic acids, nitriles and hydrocarbon monomers can be copolymerized with the Michael adducts of N-vinylformamide to produce a variety of polymers. Examples of ethylenically unsaturated monomers include esters of acrylic acid and methacrylic acid which are derived from alcohols of 1 to 18 carbon atoms. Examples of suitable alcohols for the preparation of these esters are methanol, ethanol, propanol, isopropanol, n-, i- and tert-butyl alcohol, neopentyl alcohol, 2-ethyl-hexanol, n and i-octanol, dodecanol, palmityl alcohol and stearyl alcohol. Preferably acrylic esters are those derived from alcohols of 1 to 8 carbon atoms and include methyl methacrylate, butyl acrylate, and 2-ethylhexyl acrylate. Others include hydroxy esters which are prepared by esterifying a dihydric $C_2$–$C_4$-alcohol with acrylic acid or methacrylic acid in a molar ratio of 1:1; i.e., hydroxyethyl acrylate, hydroxyethyl methacrylate, hydroxypropyl acrylate, hydroxypropyl methacrylate, hydroxybutyl acrylate and hydroxybutyl methacrylate. Examples of amides include acrylamide, methacrylamide, N-vinylacetamide, N-methylolacrylamide, etc. while nitriles include acrylonitrile and methacrylonitrile. Examples of unsaturated acids include acrylic and methacrylic acid and crotonic acid. Ethylene is the preferred hydrocarbon monomer. Other suitable monomers include N-vinylpyrrolidone, vinyl chloride and triallylcyanurate. Esters of dicarboxylic acids such as esters of $C_{1-12}$ alcohols with maleic, fumaric, itaconic acid, e.g., dioctyl maleate, may be polymerized with the monomer.

A copolymer based upon vinyl acetate and the Michael adduct of N-vinylformamide is an example of copolymers having a variety of uses. The copolymers may contain from about 1 to 95% by weight of vinyl acetate and the balance containing which is a Michael adduct of N-vinylformamide. A typical composition is a vinyl acetate/ethylene/Michael adduct of N-vinylformamide copolymer having from about 10 to 80% by weight vinyl acetate, 5–40%, more preferably 10–30% by weight ethylene and the balance being Michael adducts of N-vinylformamide. Possibly other comonomers, e.g., an acrylate ester may be added or substituted for ethylene or used in place of, or in conjunction with vinyl acetate and ethylene, thus forming an acrylic type copolymer, the sum of the percentages in the copolymers always being 100. An advantage is that the level of Michael adducts of N-vinylformamide based upon acrylate and methacrylate esters can be increase well above that normally used in vinyl acetate polymerizations. Acrylics, because of their much faster polymerization rate vis-à-vis vinyl acetate, are difficult to incorporate in high concentration. The acrylates are added as a delay in order to enhance random incorporation of the acrylic functionality in the vinyl acetate containing polymer. Through the use of the Michael adduct, incorporation of the acrylate functionality into vinyl polymers is easy due to similar polymerization rates of the vinyl monomers and the resulting polymer can accommodate levels in the range of 5 to 95% by weight.

The Michael adducts also may be homopolymerized or copolymerized with other Michael adducts to produce an aqueous emulsion. Examples of homopolymers include poly(ethylhexyl 3-(N-vinylformamido)propionate); poly(isobornyl 3-(N-vinylformamido)propionate); poly-(tert-butyl 3-(N-vinylformamido)propionate); and copolymers formed from the respective Michael adducts.

One of the advantages of the resulting polymer incorporating the Michael adduct is that it can be hydrolyzed to from a secondary amine functional group. That site may be used as a crosslinkable site for other groups such as epoxy resins, isocyanates and so forth.

Emulsion polymerization of ethylenically unsaturated monomers such as vinyl acetate is well known and conventional emulsion polymerization processes can be used to form the unique copolymers incorporating the Michael adducts described. Emulsion polymerization of the Michael adducts of N-vinylformamide with ethylenically unsaturated monomers, e.g., vinyl esters and particularly vinyl acetate, is effected in an aqueous medium under pressures generally not exceeding 1000 atmospheres in the presence of a catalyst (initiator) and at least one emulsifying agent, the aqueous system being maintained by a suitable buffering agent, within a preselected pH range, typically within a pH of from about 3 to 6. The emulsion polymerization process may be a batch process which involves a homogenization period in which a portion of the monomer is suspended in water and is thoroughly agitated in the presence of a comonomer such as ethylene while the system is gradually heated to polymerization temperature. The homogenization period is followed by a polymerization period during which the initiator system, which consists of generally of a peroxide and an activator; (as described in the literature), which are added incrementally. Alternatively, the emulsion polymerization process can rely on incremental addition of the monomers in order to produce a copolymer having a desirable distribution of the comonomers. In that case, water and the stabilizing system are added to the reactor with the monomers being added incrementally (delay addition) over time. The catalyst system comprising the oxidizing agent and reducing agent or thermal initiator are added to maintain a preselected reaction rate.

Various free-radical forming initiators such as peroxide compounds can be used in carrying out the emulsion polymerization of the monomers. Combination-type initiators employing both reducing agents and oxidizing agents can also be used. The use of this type of combined initiator is generally referred to in the art as "redox polymerization" or "redox system." The reducing agent is also often referred to as an activator and the oxidizing agent as an initiator. Suitable reducing agents or activators include bisulfites, sulfoxylates, or other compounds having reducing properties such as ferrous salts and ascorbic acid, and tertiary aromatic amines, e.g., N,N-dimethylaniline. The oxidizing agents or initiators include hydrogen peroxide, organic peroxides such as benzoyl peroxide, t-butyl hydroperoxide. A specific combination-type initiator or redox system which can be used is hydrogen peroxide and sodium formaldehyde sulfoxylate. Thermal initiators include persulfates, such as ammonium or potassium persulfate, or perborates, peracid anhydrides, percarbonates azo compounds, peresters and the like.

The initiator is employed in the amount of 0.1 to 2%, preferably 0.25 to 0.75%, based on the weight of monomer introduced into the system. The activator is ordinarily added as an aqueous solution and the amount of activator is generally from 0.25 to 1 times the amount of initiator.

A wide variety of emulsifying agents can be used in effecting emulsion polymerization of monomer systems incorporating the Michael adducts of N-vinylformamide. Typically, nonionic and anionic surfactants are used to stabilize the emulsion polymers, but also cationic surfactants can be used. Since the reactive monomer is in a neutral form during the copolymerization, no special consideration is needed regarding the compatibility with the stabilizing medium chosen for the reaction.

Suitable non-ionic emulsifying agents include polyoxyethylene condensates. Polyoxyethylene condensates may be represented by the general formula:

where R is the residue of a fatty alcohol containing 10–18 carbon atoms, an alkyl phenol, a fatty acid containing 10–18 carbon atoms, an amide, an amine, or a mercaptan, and where n is an integer of 1 to 50 or above. Some specific examples of polyoxyethylene condensates which can be used include polyoxyethylene aliphatic ethers such as polyoxyethylene lauryl ether, polyoxyethylene oleyl ether, polyoxyethylene hydroabietyl ether and the like; polyoxyethylene alkaryl ethers such as polyoxyethylene nonylphenyl ether, polyoxyethylene octylphenyl ether and the like; polyoxyethylene esters of higher fatty acids such as polyoxyethylene laurate, polyoxyethylene oleate and the like as well as condensates of ethylene oxide with resin acids and tall oil acids; polyoxyethylene amide and amine condensates such as N-polyoxyethylene lauramide, and N-lauryl-N-polyoxyethylene amine and the like; and polyoxyethylene thioethers such as polyoxyethylene n-dodecyl thioether.

One class of non-ionic emulsifying agents which can be used include a series of surface active agents known as "Pluronics." The "Pluronics" have the general formula:

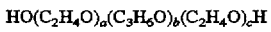

where a, b, and c are integers of 1 or above. As b increases, the compounds become less water soluble or more oil soluble and thus more hydrophobic when a and c remain substantially constant.

Some examples of non-ionic emulsifying agents sold under the Pluronic trademark which can be used include polyoxyethylene-polyoxypropylene glycols conforming to the above general formula for "Pluronics" in which the polyoxypropylene chain has a molecular weight of 1500 to 1800 and the polyoxyethylene content is from 40 to 50 percent of the total weight of the molecule, a polyoxypropylene having a cloud point of about 140° F. and marketed under the trademark "Pluronic L-64"; a polyoxyethylene-polyoxypropylene glycol conforming to the above general formula for "Pluronics" in which the polyoxypropylene chain has a molecular weight of 1500 to 1800 and the polyoxyethylene content is from 80 to 90 percent of the total weight of the molecule and having a cloud point of about 212° F. and marketed under the trade mark "Pluronic F-68". "Pluronics" are obtained by condensing ethylene oxide on the polyoxypropylene base and the hydrophobic-hydrophilic nature of the resulting compound is controlled by varying the molecular weight of either the hydrophobic base or the hydrophilic portion of the molecule.

Another class of nonionic surfactants are sold under the Igepal trademark. One example within this class is a polyoxyethylene nonylphenyl ether having a cloud point of between 126° and 133° F. and marketed under the trade mark "Igepal CO-630"; another is polyoxyethylene nonylphenyl ether having a cloud point above 212° F. and marketed under the trade mark "Igepal CO-887." A similar polyoxyethylene nonylphenyl ether with a cloud point of about 86° F. is marketed under the trade mark "Igepal CO-610." Surfactants similar to the Igepal surfactants include a polyoxyethylene octylphenyl ether having a cloud point of between 80° F. and 160° F. marketed under the trademark "Triton X-100", a polyoxyethylene oleyl ether having a cloud point of between 80° F. and 160° F. marketed under the trade mark "Atlas G-3915" and a polyoxyethylene lauryl ether having a cloud point above 190° F. marketed under the trademark "Brij 35."

A protective colloid also can be used in the polymerization mixture as a stabilizing agent. Various colloids and amounts conventionally used in emulsion polymerization can be incorporated into the latices as desired and in combination with the surfactants. Representative colloids which can be used include polyvinyl alcohol, partially-acetylated polyvinyl alcohol, e.g., up to 50% acetylated, casein, hydroxyethyl starch, carboxymethylcellulose, gum arabic, and the like.

The concentration range of the total amount of stabilizing agents used in emulsion polymerization is from 0.5 to 10% based on the aqueous phase of the latex regardless of the solids content. The stabilizers employed are, in part, governed by the use to which the copolymer latex is to be put. By utilizing appropriate levels of surfactant and/or protective colloid, one can obtain latex polymer particles having a variety of average particle size ranges and distributions.

In order to maintain the pH of the system at the desired value, there is suitably added a buffering agent of any convenient type. Any alkaline material which is compatible with the stabilizing agent can be used as the buffer. The amount of buffer is that sufficient to adjust the pH of the system within the desired range, e.g., 2.5 to 10 and preferably 3.0–7.0.

Reaction temperatures for emulsion polymerizing Michael adducts of N-vinylformamide along with other monomers such as vinyl acetate, for example, are conventional. The reaction temperature can be controlled by the rate of catalyst addition and by the rate of the heat dissipation therefrom. Generally, it is advantageous to maintain a temperature from about 50° to 90° C. While temperatures as low as 0° C. can be used, economically, the lower temperature limit is about 40° C.

The reaction time will also vary depending upon other variables such as the temperature, the catalyst, and the desired extent of the polymerization. It is generally desirable to continue the reaction until less than 0.5% of the Michael adduct of NVF or vinyl acetate, if employed, remains unreacted. Under these circumstances, a reaction time of about 4–6 hours has been found to be generally sufficient for complete polymerization, but reaction times ranging from 3 to 10 hours have been used, and other reaction times can be employed, if desired.

Emulsion polymerization can also be conducted in the presence of a polymer such as a water dispersible polyurethane to produce a polyurethane/Michael adduct hybrid. Conventional diisocyanates and polyols may be used to produce the polyurethanes.

The following examples illustrate synthesis of the Michael adducts and their incorporation into latex emulsions and applications thereof.

EXAMPLE 1

Preparation of Methyl 3-N-Vinylformamidopropionate

To a 1000 ml three-neck round bottom flask equipped with a cold water condenser and stirrer was added 215 grams (2.5 moles) methyl acrylate, 195 grams (2.75 moles)

N-vinylformamide, and 0.1 grams benzoquinone. The mixture was stirred at ambient temperature for two minutes and 1.5 grams sodium methoxide was added in one portion. The mixture was stirred for approximately 2 hours at ambient temperature and allowed to stand overnight. The reaction mixture was distilled under vacuum and 361 grams of product (92% yield) boiling at 75° C. (0.8 mm Hg) was collected for analysis. $^1$H NMR analysis confirmed the identity of the 3-N-vinylformamido adduct.

EXAMPLE 2

Preparation of Ethyl 3-N-Vinylformamidopropionate

To a 100 ml three-neck round bottom flask equipped with a cold water condenser and stirrer was added 30.9 grams of ethyl acrylate and 21.9 grams of NVF. After mixing for 2 minutes, 0.20 grams of sodium methoxide was added in one portion. The mixture was allowed to react for 3 hours and then distilled to recover 40.3 grams of product boiling at 88° C. (1.0 mm Hg).

EXAMPLE 3

Preparation of Butyl 3-N-Vinylformamidopropionate 72.5 grams of n-butyl acrylate were reacted with 43.0 grams of NVF according to the procedure of Example 2. The mixture was allowed to react for 4 hours and then distilled to recover 101.2 grams of product boiling at 96° C. (0.5 mm Hg).

EXAMPLE 4

Preparation Of tert-Butyl 3-N-Vinylformamidopropionate 21.9 grams of t-butyl acrylate were reacted with 42.0 grams of NVF according to the procedure of Example 2. The mixture was allowed to react for 72 hours and then distilled to recover 51.5 grams of product boiling at 80° C. (0.5 mm Hg).

EXAMPLE 5

Preparation Of Ethylhexyl 3-N-Vinylformamidopropionate 83.1 grams of 2-ethylhexyl acrylate were reacted with 34.4 grams of NVF according to the procedure of Example 2. The mixture was allowed to react for 96 hours and then distilled to recover 79.8 grams of product boiling at 122° C. (0.8 mm Hg).

EXAMPLE 6

Preparation Of Methyl 2-Methyl-3-N-Vinylformamidopropionate

To a 100 ml three neck round bottom flask equipped with a cold water condenser, oil bath and stirrer was added 33.2 grams of methyl methacrylate and 23.6 grams of NVF. The mixture was stirred at room temperature for 2 minutes and 80 mg of butyl lithium (as a 2.5M solution in hexane) was added in a single portion. The reaction mixture was agitated for 8 hours at 65° C. and then distilled to recover 29.5 grams of product boiling at 75°–77° C. (0.5 mm Hg).

EXAMPLE 7

Preparation Of Isobornyl 3-(N-Vinylformamido) Propionate

To a 100 ml three-neck round bottom flask equipped with a cold water condenser and stirrer was added 20.8 grams of isobornyl acrylate, 0.01 gram of benzoquinone, and 7.1 grams of NVF. After mixing for 2 minutes, 0.1 gram of 25% sodium methoxide in methanol solution was added in one portion. After stirring at ambient temperature for 20 hours, the colored mixture was distilled and a fraction at 143°–145° C./0.7 mmHg was collected to give 22.3 grams of colorless isobornyl 3-(N-vinylformamido)propionate (80%).

EXAMPLE 8

Preparation Of Benzyl 3-(N-Vinylformamido) propionate

To a 100 ml three-neck round bottom flask equipped with a cold water condenser and stirrer was added 14.6 grams of benzyl acrylate, 0.01 gram of benzoquinone, and 7.1 grams of NVF. After mixing for 2 minutes, 0.1 gram of 25% sodium methoxide in methanol solution was added in one portion. After stirring at ambient temperature for 24 hours, the colored mixture was distilled and a fraction at 147°–148° C./0.8 mmHg was collected to yield 16.5 grams of benzyl 3-(N-vinylformamido)propionate as a pale yellow liquid (76%).

EXAMPLE 9

Preparation Of N,N-Dimethylaminoethyl 3-(N-Vinylformamido)propionate

To a 100 ml three-neck round bottom flask equipped with a cold water condenser and stirrer was added 14.3 grams of N,N-dimethylaminoethyl acrylate, 0.01 gram of benzoquinone, and 7.1 grams of NVF. After mixing for 2 minutes, 0.1 gram of 25% sodium methoxide methanol solution was added in one portion. After stirring at ambient temperature for 24 hours, the colored mixture was distilled and a fraction at 115°–120° C./1 mmHg was collected to yield 12.2 grams of N,N-dimethylaminoethyl 3-(N-vinylformamido)propionate as a pale yellow liquid (57%).

EXAMPLE 10

Preparation Of 2,2,3,4,4,4-Hexafluorobutyl 3-(N-Vinylformamido)propionate

To a 100 ml three-neck round bottom flask equipped with a cold water condenser and stirrer was added 23.6 grams of 2,2,3,4,4,4-hexafluorobutyl acrylate, 0.01 gram of benzoquinone, and 7.1 grams of NVF. After mixing for 2 minutes, 0.2 gram of 25% sodium methoxide methanol solution was added in one portion. After stirring at ambient temperature for 24 hours, the color mixture was distilled and fraction at 95° C./0.5 mmHg was collected to yield 14.3 grams of 2,2,3,4,4,4-Hexafluorobutyl-3-(N-vinylformamido)propionate as a pale yellow liquid (47%).

EXAMPLE 11

Preparation Of Allyl 3-(N-Vinylformamido) propionate

To a 250 ml three-neck round bottom flask equipped with a cold water condenser and stirrer was added 82.2 grams of allyl acrylate, 0.01 gram of benzoquinone, and 57.3 grams of NVF. After mixing for 2 minutes, 0.2 gram of 25% sodium methoxide methanol solution was added in one portion. After stirring at 60° C. for 24 hours, the colored mixture was distilled and a fraction distilled at 100°–110° C./1 mmHg was collected to yield 53.0 grams of allyl 3-(N-vinylformamido)propionate as a pale yellow liquid (38%).

PREPARATION OF LATEX EMULSION

In affecting polymerization of the Michael adducts of N-vinylformamide in conjunction with other monomers, all reactions were carried out in glass or stainless steel reactors which were equipped with agitators, thermocouples, and ports for the addition of raw materials. The reactors had jackets through which was circulated tempered water to maintain the proper reaction temperature. All polymerizations were conducted under a nitrogen atmosphere and all water used in the emulsion polymerizations was de ionized.

Latex viscosities were measured on a Brookfield model LTV viscometer unless otherwise specified. Non-volatile content of the latex was determined by drying weighed amounts of the latex in a 150° C. oven for 30 minutes.

EXAMPLE 12

Vinyl Acetate-Co-Methyl 3-(N-Vinylformamido) propionate Polymer Dispersion

To a 2 liter glass reactor was charged 612 grams of water, 82.5 grams of a 2% non-volatiles solution of Natrosol™ 250 GR (Natrosol is a modified cellulose manufactured by Hercules, Inc.), 20.9 g of Igepal™ CO-887, 10.5 grams of Igepal™ CO-630 (CO-887 and CO-630 are ethoxylated nonylphenols manufactured by Rhone-Poulenc Inc.), and 2 grams of a 5% solids solution of ferric ammonium sulfate.

A monomer mixture was prepared comprising 690 grams of vinyl acetate, 115 grams methyl 3-(N-vinylformamido)-propionate, 16 grams Pluronic™ F-68, 9.8 grams of Pluronic™ F-64 (F-68 and F-64 are polyethylene oxide/polypropylene oxide block copolymers manufactured by BASF Wyandotte Corp.), and 0.94 grams of 70% t-butyl hydroperoxide. An activator solution consisted of 0.78 grams sodium formaldehyde sulfoxylate, 0.78 grams of sodium benzoate, and 30.4 grams of water.

The reactor was purged with nitrogen and 48.8 grams of monomer mixture was added. Reactor contents were heated to 65° C. and 1.7 grams of activator solution was added. Polymerization was initiated and mixture exothermed to 66.9° C. After initiation, the remaining monomer mixture and activator solution were added over 110 minutes, while maintaining temperature at 65° C. When residual vinyl acetate was <0.5%, the reaction mixture was cooled and filtered. Physical properties are summarized in Table 1.

EXAMPLE 13

Vinyl Acetate-Co-Butyl 3-(N-Vinylformamido) propionate Polymer Dispersion

The procedure and composition for this Example 13 was identical to Example 12 except that butyl 3-(N-vinylformamido)propionate was substituted for methyl 3-(N-vinylformamido)propionate. The physical properties are summarized in Table 1.

EXAMPLE 14

Vinyl Acetate-Co-Methyl 2-Methyl-3-(N-Vinylformamido)propionate Polymer Dispersion The procedure and composition was identical to Example 13 except that methyl 2-methyl-3-(N-vinylformamido) propionate was substituted for methyl 3-(N-vinylformamido)propionate. Physical properties are summarized in Table 1.

TABLE 1

Physical Properties

| Example | % non-volatile | pH | Viscosity (cps) #2 spindle @ 60 rpm | Tg(°C.) |
|---|---|---|---|---|
| 12 | 53 | 3.6 | 800 | 33.5 |
| 13 | 50 | 3.0 | 260 | 10.7 |
| 14 | 52.3 | 4.3 | 235 | 18.6 |

Table 1 shows the effect of the particular Michael adduct of N-vinylformamide on the Tg of the resulting polymer.

EXAMPLE 15

Latex Based Paints

The Example 13 polymer dispersion was evaluated as a let down vehicle in a typical flat and a semi-gloss paint.

| Pigment Pastes Typical Semi-gloss base | grams | Typical Flat base | grams |
|---|---|---|---|
| Texanol ™ 14 g | 14 | Natrosol ™ 250HR (2% solution) | 100 |
| Propylene glycol | 35 | Amp ™ 95 | 3 |
| Tamol ™ 731 | 4 | Ethylene glycol | 20 |
| Foamester ™ | 44 | Texanol ™ | 5 |
| Amp ™ 95 | 2 | Igepal ™ CO610 | 3 |
| TiPure ™ R900 | 250 | Drew ™ L475 | 2 |
| Kathon ™ LX | 1 | Tamol ™ 850 | 5 |
| Water | 40 | TiPure ™ R901 | 200 |
| Aerosol ™ OT | 1.5 | Satintone ™ #w | 50 |
| Foamester ™ 44 | 2 | Al Silate ™ NC | 75 |
| Natrosol ™ 250MR (3% solution) | 75 | Snowflake ™ | 50 |
|  |  | Goldbond ™ R | 75 |
|  |  | Nuosept ™ T | 1 |
|  |  | Water | 55 |
|  |  | Natrosol ™ 250HR (2% solution) | 175 |
|  |  | Drew ™ L475 |  |
| Letdown Formula |  |  |  |
| Semi-gloss Paint |  | Flat Paint |  |
| Semi-gloss paste | 437.5 g | Flat paste | 824 g |
| Water | 71 | Water | 104 |
| Natrosol ™ 250MR (3% solution) | 100 | Texanol ™ | 3 |
| Example 13 polymer dispersion | 420 | Example 13 polymer dispersion | 230 |

The viscosity response in both flat and semi-gloss paints was better with the Example 13 polymer dispersion than with a conventional vinyl acetate co-butyl acrylate polymer dispersion. The gloss development in the semi-gloss paint made with the Example 13 polymer dispersion was significantly improved. This may be the result of random distribution of acrylate type functionality into the polymer due to the similarity in polymerization rates of the vinyl acetate and Michael adduct monomers.

EXAMPLE 16

Vinyl Acetate-Co-Butyl 3-(N-Vinylformamido) propionate -Co-Ethylene Polymer Dispersion To a one gallon stainless steel reactor equipped for pressure emulsion polymerization was charged 400 grams of water, 506.25 grams of a 10% solution of Airvol™ 205 polyvinyl alcohol, 168.75 grams of a 10% solution of Airvol™523 polyvinyl alcohol, 1150 grams of vinyl acetate, 10 grams of sodium citrate, 4.5 grams of sodium bisulfite, and 200 grams of butyl 3-(N-vinylformamido)propionate.

The following solutions were prepared: 300 grams of a 3% sodium persulfate solution and 115 grams of a 10% sodium persulfate solution.

The reactor was sealed and 290 grams of ethylene were pumped into the reactor. The reactor contents were heated to 80° C. The 3% sodium persulfate solution was added at the rate of 2.0 grams/min for 5 minutes. Initiation was noted by virtue of a 2° C. exotherm. When the temperature stabilized, the 3% sodium persulfate solution was added at a rate of 0.25 grams/min for 180 minutes. At 20 minutes into the addition, 25 grams of ethylene was pumped in. At 1 hour into the additions, the 3% sodium persulfate solution feed rate was increased to 1 gram/min. After all the initiator solution was pumped in, the reaction was held at 80° C. for 30 minutes. The 10% solution of sodium persulfate was then pumped in over 30 minutes and the reaction was held at 80° C. for an additional 30 minutes.

When the free monomer was <0.7%, the polymer dispersion was cooled to 25° C., and 7.5 grams of 14% aqueous ammonia was added. The dispersion was then transferred to the degasser. When degassed, the dispersion was filtered through a 100 mesh bag and physical properties were determined.

| Physical Properties | |
| --- | --- |
| % Non-volatile | 53.17 |
| pH | 5.56 |
| Viscosity | |
| #3 spindle @ 2 rpm | 740 cps |
| #3 spindle @ 60 rpm | 376 |
| #2 spindle @ 20 rpm | 464 |

EXAMPLE 17

Butyl Acrylate-Co-Methyl Methacrylate-Co-Methacrylic Acid -Co-N-Butyl 3-(N-Formamido) propionate Polymer Dispersion First Stage Polymerization To a 2 liter reactor was charged 735 grams water. The water was heated to 80° C. and a solution of 7.5 grams of ammonium persulfate in 60 grams of water was added to the reactor. Then a mixture comprising 124.5 grams of methyl methacrylate, 273.8 grams of butyl acrylate, 105 grams of methacrylic acid, 146.6 grams of α-methyl styrene, and 13 grams of dodecyl mercaptan were added to the reactor uniformly over a 2 hour period.

The polymer dispersion was then held at 85° C. for 30 minutes, and a solution of 0.75 grams of ammonium persulfate dissolved in 15 grams water was added. The dispersion was held at 85° C. until the residual unreacted monomer was less than 1000 ppm. The dispersion was cooled to room temperature and the pH was adjusted to 5.5 by the addition of 28% aqueous ammonia. The dispersion contained 45% non-volatiles.

Polymer Dispersion

To a 2 liter reactor was charged, 167.6 grams of first stage polymer dispersion and 340.9 grams water. A monomer mixture comprising 367.5 grams of butyl acrylate, 375 grams of methyl methacrylate, 7.5 grams of methacrylic acid, and 28.5 grams of n-butyl 3-(N-vinylformamido)-propionate. An initiator solution was prepared from 3 grams of ammonium persulfate, 7.5 grams sodium bicarbonate, and 75 grams of water. Fifteen grams of the monomer mixture were added to the reactor and the reactor then heated to 65° C. Five grams of the initiator solution was added and heating continued to 76° C. While maintaining the temperature at 76° C., the remaining monomer mixture and initiator solution were pumped in over a 3 hour period. The reaction mixture was then held at 76° C. for 30 minutes. The temperature was then raised to 80° C. and a solution of 0.75 grams of ammonium persulfate in 15 grams of water was added all at once. Heating was continued until the residual monomer was less than 1000 ppm.

The polymer dispersion was cooled to room temperature, filtered through a 100 mesh bag, and the physical properties determined.

| Physical Properties | |
| --- | --- |
| % Non volatiles | 61.19 |
| pH | 6.77 |
| Viscosity (#3 spindle @ 30 rpm) | 1328 cps |
| (#3 spindle @ 60 rpm) | 856 |

The polymer dispersion when compounded with pigment and melamine-formaldehyde was useful as a coil coating.

EXAMPLE 18

Butyl Acrylate-Co-2-Hydroxypropyl Acrylate-Co-Acrylic Acid -Co-2-Ethylhexyl 3'-(N-Vinylformamido)propionate Polymer Dispersion First Stage Polymerization De-ionized water (440 grams) was charged to a 2 liter glass reactor. A monomer emulsion was prepared from 460 grams of de-ionized water, 10 grams of Abex JKB (a proprietary alcohol ether sulfate surfactant manufactured by Rhone-Poulenc Inc.), 416 grams of 2-ethylhexyl acrylate, 148 grams of methacrylic acid, 12 grams of acrylic acid, 64 grams of vinyl acetate, and 20 grams of dodecyl mercaptan. An initiator solution was prepared from 10 grams ammonium persulfate and 40 grams water. The reactor contents were heated to 80° C., and the initiator solution was added all at once. The monomer emulsion was then pumped in over a two hour period. After completion of the addition, the dispersion was held at 80° C. for 30 minutes. The dispersion was then heated to 90° C. and a solution of 1 grams of ammonium persulfate in 10 grams of water was added all at once to convert any residual monomer to polymer. When the residual was less than 1000 ppm, the mixture was cooled, filtered through a 100 mesh bag, and the pH adjusted to 5.5 with 28% aqueous ammonia.

| Physical Properties | |
| --- | --- |
| % Non-volatile | 39.65% |
| Viscosity (#3 spindle @ 30 rpm) | 376 cps |
| (#3 spindle @ 60 rpm) | 260 |

2nd Stage Polymerization

A 2 liter reactor was charged with 178.6 grams of first stage polymer and 140 grams of de-ionized water. An initiator solution was prepared from 1.8 grams of sodium persulfate, 3 grams of sodium bicarbonate, and 50 grams of water. A monomer emulsion was prepared from 140 grams of water, 46.08 grams of Abex JKB, 19.2 grams of sodium vinyl sulfonate solution (25% solids), 3.2 grams of acrylic acid, 576 grams of butyl acrylate, 19.2 grams of hydroxypropyl acrylate, and 64 grams of 2-ethylhexyl 3'-(N-vinylformamido)-propionate.

To the reactor were added 15 grams of monomer emulsion and the reactor contents heated to 65° C. At 65° C., 5 grams of the initiator solution was added and heating continued to 76° C. When the temperature was reached, the remaining monomer emulsion and initiator solution were added over a 2 hour period. When the additions were completed, the dispersion was held at 76° C. for 15 minutes, and the temperature then raised to 80° C. A solution of 0.8 grams of sodium persulfate dissolved in 10 grams of water was added all at once in order to polymerize any residual monomer. When the residual monomer was less than 1000 ppm, the polymer dispersion was cooled, filtered through a 100 mesh bag, and the physical properties were determined.

| Physical Properties | |
| --- | --- |
| % Non-volatile | 59.65 |
| pH | 5.80 |
| Viscosity (#3 spindle @ 30 rpm) | 800 cps |
| (#3 spindle @ 60 rpm) | 512 |

Adhesive Preparation

The polymer dispersion was tested as a pressure sensitive adhesive using standard Pressure Sensitive Tape Council methods. The dispersion was coated on Polyslik™ release paper (a siliconized, polyethylene coated paper) and dried. The adhesive coated paper was laminated to a 2 mil polyester film. The adhesive transferred to the film. The adhesive deposit level on the film was 25 g/m².

| Test | Value |
| --- | --- |
| PSTC #1. 180° peel adhesion | 228 N/m |
| PSTC #7. 178° shear adhesion (1.6 cm², 500 grams load) | 1.5 hrs. |
| Loop tack* | 175 N/m |

The loop tack was measured using a 2.54×20.32 cm strip of adhesive coated film into a loop and applied across a 2.54 cm wide stainless steel panel with minimal pressure so that the contact area was 6.45 cm² ( one square inch), thus the panel was perpendicular to the length of the adhesive strip. The strip is then pulled away from the panel at an angle of 90° at a rate of 30.48 cm per minute using an Instron™ tester. These results show that excellent pressure sensitive adhesives can be prepared using the Michael adduct of N-vinylformamide which incorporates acrylate type functionality. The results are comparable to an all acrylate system.

What is claimed is:

1. In an aqueous emulsion comprising a polymer containing polymerized units of an ethylenically unsaturated monomer, the improvement which comprises the incorporation of polymerized units of Michael adducts of N-vinylformamide in said polymer, said Michael adducts of N-vinylformamides represented by the formula:

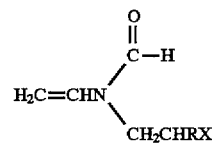

where R is H or $CH_3$, X=CN, $O=CR_1$, $O=COR_1$, $O=CNR_1R_1$ wherein $R_1$ is a linear or branched alkyl, and fluorinated alkyl 3-N-vinylformamido propionates and fluorinated 2-methyl- 3-N-vinylformamido propionates, cycloalkyl, heterocyclic, arylalkyl, alkyloxy or aryl group containing between 1 and about 20 carbon atoms.

2. The aqueous emulsion of claim 1 in which $R_1$ is C1–12 alkyl.

3. The aqueous emulsion of claim 2 in which $R_1$ contains from 1 to 8 carbon atoms.

4. The aqueous emulsion of claim 3 where X is $O=COR_1$.

5. The aqueous emulsion of claim 4 in which at least one comonomer is polymerized with said Michael adduct of N-vinylformamide and said monomer is selected from the group consisting of $C_{1-8}$ alkyl vinyl ester and a $C_{1-10}$ alkyl ester of acrylic or methacrylic acid.

6. The aqueous emulsion of claim 5 wherein the vinyl ester is vinyl acetate and the polymer contains from 10 to 80% by weight vinyl acetate.

7. The aqueous emulsion of claim 6 wherein the polymer contains from 5 to 40% ethylene.

8. The aqueous emulsion of claim 5 wherein the polymer contains from 5 to 95% by weight of a $C_{1-8}$ alkyl ester of acrylic or methacrylic acid.

9. In an aqueous latex emulsion comprising polymerized units of an ethylenically unsaturated monomer, the improvement which comprises a polymer having polymerized units of a Michael adduct of N-vinylformamide incorporated therein, said Michael adduct having the structure:

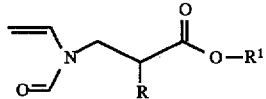

where R of the Michael adduct is an allyl group or benzyl group and $R^1$ is an alkyl group, fluorinated alkyl 3-N-vinylformamido propionates and fluorinated 2-methyl- 3-N-vinylformamido propionates where the alkyl group has from 1–12 carbon atoms.

10. In the aqueous latex emulsion of claim 1 comprising polymerized units of an ethylenically unsaturated monomer, the improvement which comprises a polymer having polymerized units of a Michael adduct of N-vinylformamide incorporated therein, said Michael adduct having the structure:

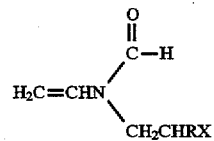

wherein R is H and X=CN.

* * * * *